United States Patent [19]

Bose et al.

[11] Patent Number: 4,856,320

[45] Date of Patent: Aug. 15, 1989

[54] METHOD AND APPARATUS FOR MEASURING PHYSICAL ADSORPTION OF GASES BASED ON DIELECTRIC MEASUREMENTS

[75] Inventors: Tapan K. Bose; Richard Chahine; Louis Marchildon; Jean-Marie St-Arnaud, all of Trois-Rivières, Canada

[73] Assignee: Universite du Quebec a Trois-Rivieres, Societe Quebecoise d'Initiatives Petrolieres and Gaz Metropolitain Inc., Quebec, Canada

[21] Appl. No.: 241,844

[22] Filed: Sep. 8, 1988

[51] Int. Cl.$^4$ .............................................. G01N 9/00
[52] U.S. Cl. ......................................................... 73/30
[58] Field of Search ............................................ 73/30

[56] References Cited

FOREIGN PATENT DOCUMENTS 926563  5/1982  U.S.S.R. .................................... 73/30

Primary Examiner—Tom Noland
Assistant Examiner—Josesph W. Roskos
Attorney, Agent, or Firm—Charles E. Brown; Charles A. Brown

[57] ABSTRACT

A method and apparatus for measuring physical adsorption of a gas by a solid adsorbent are disclosed. Use is made of a capacitance cell in controlled gas flow communication with a sample cell initially under vacuum and containing the solid adsorbent. The capacitance cell is filled with an adsorptive gas at a predetermined pressure and the dielectric constant of the gas at the predetermined pressure is measured to determine a first density value. The gas from the capacitance cell is then allowed to expand into the sample cell for adsorption by the solid adsorbent, whereby an adsorption takes place pressure falls until eqilibrium is established. The dielectric constant of the gas at equilibrium pressure is measured to determine a second density value, and the amount of gas adsorbed by the solid adsorbent is determined from the first and second density values.

19 Claims, 2 Drawing Sheets

METHOD AND APPARATUS FOR MEASURING PHYSICAL ADSORPTION OF GASES BASED ON DIELECTRIC MEASUREMENTS

The present invention relates to gas adsorption measurements. More particularly, the invention is concerned with a method and apparatus for measuring physical adsorption of a gas by a solid adsorbent.

Physical adsorption of a gas by a solid is the condition in which the concentration of the gas molecules at the gas/solid interface is greater than the bulk concentration. This enrichment is caused by the van der Waals interactions at the gas/solid interface. The nature of the solid plays an important role in adsorption phenomena. In general, the atoms in the solid are distributed in a periodic crystalline structure, and the total force exerted by the solid atoms on a gaseous molecule depends very much on the position of the gas molecule on the solid surface. Certain sites in the solid surface are more favorable to adsorption than others.

For a given mass of solid, the adsorption goes up with the amount of surface available. Maximization of surface for a given mass may be realized either by breaking up the solid into fine particles or, more realistically, by producing an extensive network of fine pores in the solid. The adsorption properties of a porous solid depend on the size of its pores. The pore sizes classified as micropores (<2 nm) are mostly responsible for pore filling adsorption. The bigger pore sizes like mesopores (between 2 and 50 nm) and macropores (>50 nm) are responsible for monolayer/multilayer adsorption and capillary condensation.

The adsorption studies at high pressures and high temperatures have important industrial applications in the fields of separation and purification of hydrogen, light hydrocarbons and several other gases, storage of fuel gases in microporous solids, catalytic reactions, and chromatography. The measurement of adsorption at the gas/solid interface also serves as an essential tool in the study of solid surfaces and the characterization of microporous materials.

Although numerous instruments exist to measure gas adsorption at low pressures, those capable of operating at high pressures are rare and necessitate specialized construction. The high-pressure adsorption measurements have been essentially based on standard volumetric and gravimetric principles.

In the volumetric method, the adsorbate gas of known pressure and volume is allowed to expand into a cell containing the sample. If the sample dead space is known, the amount of adsorption can be found by the application of the gas laws. This method is reliable at low pressure where all gases in the bulk phase closely resemble the ideal gas. At high pressure, however, where the gas phase deviates significantly from ideality, the reliability of the volumetric method is very much dependent upon the availability and the accuracy of the compressibility data for the gas of interest. This is due to the fact that the adsorbed amount is calculated from the density of the gas which in turn is derived from the experimentally measured pressure and the compressibility data for the gas. As an example, a 3% deviation from ideality can modify the amount of adsorption increments by 50% to 100% because the calculated amount is a small difference between two large numbers.

In the gravimetric method, the amount of gas adsorbed is directly measured by the change in weight of the adsorbent using a microbalance. Depending on the type of balance used, the great uncertainty factor in gravimetric measurement of adsorption at high pressures arises from the buoyancy correction to be applied to the observed results. This correction could be as large as the weighted amounts. Moreover, the gravimetric method is limited to 15 MPa and it is especially convenient for measurements with vapors at temperatures not far removed from ambient. At both high and low temperatures, however, it becomes difficult to control and measure the exact temperature of the adsorbent.

It is therefore an object of the present invention to overcome the above drawbacks and to provide a method and apparatus enabling precise measurement of gas adsorption at high pressures.

In accordance with one aspect of the invention, there is provided a method of measuring physical adsorption of a gas by a solid adsorbent, wherein use is made of a capacitance cell in controlled gas flow communication with a sample cell initially under vacuum and containing the solid adsorbent. The method of the invention comprises the steps of:

(a) filling the capacitance cell with an adsorptive gas at a predetermined pressure and measuring the dielectric constant of the gas at the predetermined pressure to determine a first density value;

(b) allowing the gas from the capacitance cell to expand into the sample cell for adsorption by the solid adsorbent, whereby as adsorption takes place pressure falls until equilibrium is established;

(c) measuring the dielectric constant of the gas at equilibrium pressure to determine a second density value; and (d) determining the amount of gas adsorbed by the solid adsorbent at the equilibrium pressure from the first and second density values.

The present invention also provides, in another aspect thereof, an apparatus for measuring physical adsorption of a gas by a solid adsorbent, comprising:

a capacitance cell having therein at least two electrode members arranged in opposite spaced-apart relation to one another, the electrode members being provided with connector means for connection to a capacitance bridge;

a sample cell for containing the solid adsorbent;

conduit means interconnecting the cells for allowing gas flow communication therebetween, the conduit means being provided with valve means for controlling the gas flow between the cells;

vacuum means connected to the sample cell for evacuating same; and gas compressing means connected to the capacitance cell for filling same with an adsorptive gas at a predetermined pressure, whereby the adsorptive gas from the capacitance cell is allowed to expand into the sample cell for adsorption by the solid adsorbent and the dielectric constant of the gas is measured before and after expansion to determine the amount of gas adsorbed by the solid adsorbent.

For a given gas/solid system maintained at constant temperature, the amount of gas adsorbed is a function of the adsorptive pressure only. The relation between the quantity thus adsorbed and the equilibrium pressure is called the adsorption isotherm.

The method according to the invention is based on dielectric constant measurements and utilizes a capacitance cell of calibrated volume $V_c$, connected by a valve to a sample cell of volume $V_s$ and containing the solid adsorbent. Initially the capacitance cell is filled with the adsorptive gas. Its density $d_1$ is determined from the measurement of the dielectric constant $\epsilon_1$. The sample cell is under vacuum. Gas from the capacitance cell is then allowed to expand into the sample cell. As adsorption takes place, the pressure in the system falls until equilibrium is established. Measurement of the dielectric constant $\epsilon_2$ gives the equilibrium density $d_2$. The amount of gas molecules adsorbed, $N_{ad}$, is given as the difference between the amount of gas molecules admitted, N, and the amount, $N_g$, required to fill the dead space $V_g$ around the solid adsorbent. In terms of measured densities, $N_{ad}$ is given by:

$$N_{ad} = (d_1 - d_2)V_c - d_2 V_g \qquad (1)$$

Calibration of the capacitance cell volume $V_c$ can be carried out with the volumetric expansion technique using a standard volume cylinder which is evacuated. In this procedure, helium gas in the capacitance cell at an initial pressure $P_1$ of about 1 MPa is allowed to expand into evacuated cylinder. The new equilibrium pressure $P_2$ is a fraction q of $P_1$, with the value of q fixed by $V_c$.

Calibration of the dead space volume $V_g$, on the other hand, is advantageously carried out in a prior experiment with the apparatus according to the invention, by the admission in the sample cell of a reference gas, usually helium, which is adsorbed to a negligible extent ($N_{ad} \simeq 0$). In this procedure, helium in the capacitance cell at an initial density $d_1$ determined by dielectric constant measurement is allowed to expand into the vacuum of the sample cell containing the adsorbent. The new density $d_2$ is a fraction u of $d_1$. With helium adsorption being negligible, the value of u is fixed by $V_g$.

The adsorption isotherm can be constructed point by point by maintaining a balance of alternate fill-ups of the capacitance cell and expansions into the sample cell.

The relation between the gas density and its dielectric constant is given by the Clausius-Mossotti function CM which, for dielectric constant $\epsilon$, may be developed in terms of molar density d by the series:

$$CM = (\epsilon - 1)[(\epsilon + 2)d]^{-1} = A_\epsilon + B_\epsilon d + C_\epsilon d^2 \qquad (2)$$

where $A_\epsilon$, $B_\epsilon$, and $C_\epsilon$ are, respectively, the first, the second, and the third dielectric virial coefficients. The first dielectric virial coefficient $A_\epsilon$ represents the contribution of individual molecules to CM, the second dielectric virial coefficient $B_\epsilon$ represents the contribution of pairs of molecules to CM, the third dielectric virial coefficient $C_\epsilon$ represents contributions due to triplets of molecules, and so on. Measurements of $A_\epsilon$ have long been used to derive accurate values of molecular polarizabilities and dipole moments, while measurements of the higher coefficients have yielded precise values of molecular multipole moments and provided information about intermolecular interactions.

Depending on the pressure range of the experiment and the polarity of the measured gas, contributions to CM from $B_\epsilon$ and higher coefficients can be more or less significant. Keeping this in mind and the fact that determination of higher-order coefficients requires additional measurements, one can then derive separate approximations for polar and nonpolar gases.

In the pressure range of adsorption measurements for most nonpolar gases, contributions to CM from $B_\epsilon$ and higher coefficients are negligible. Thus, for all practical purposes, Eq. (2) reduces to:

$$(\epsilon - 1)(\epsilon + 2)^{-2} \approx A_\epsilon d_{68}, \qquad (3)$$

from which the first-order density approximation is given by:

$$d^{(1)} = (\epsilon - 1)/[(\epsilon + 2)A_\epsilon]. \qquad (4)$$

If measurements of $\epsilon$ are done at known pressures P, the necessary value of $A_\epsilon$ can then be obtained easily by considering the expansion of the equation of state in the form:

$$P(RTd)^{-1} = 1 + B_p d + C_p d^2 + \qquad (5)$$

where R is the universal gas constant, and $B_p$, $C_p$ are the second and third pressure virial coefficients. Eliminating d between Eqs. (2) and (5), one obtains:

$$(\epsilon - 1)(\epsilon + 1)^{-1}(RT/P) = A_\epsilon + (B_\epsilon - A_\epsilon B_p)(P/RT) + \qquad (6)$$

A plot of $(\epsilon - 1)(\epsilon + 2)(RT/P)$ vs $(P/RT)$ is a straight line with the intercept Ae and slope $(B_{\epsilon - A_\epsilon B_p})$. As will be seen later, values of $A_\epsilon$ determined by this method can be reliable to a few parts in $10^4$, being dependent only on the accuracy of the measured quantities P, T, and $\epsilon$.

It should be noted at this point that $A_\epsilon$ of nonpolar gases is temperature independent, and for a given gas it needs to be measured only once. This feature is especially helpful when adsorption measurements are carried out at different temperatures.

Contributions to CM of polar gases from $B_\epsilon$, become noticeable at lower pressure and should be taken into account. In this case, Eq. (2) is written as:

$$CM = (\epsilon - 1)/[(\epsilon + 2] \approx A_\epsilon + B_\epsilon d \qquad (7)$$

Defining a function f as:

$$f = (\epsilon - 1)(\epsilon + 2)^{-1}, \qquad (8)$$

one gets:

$$d^{(2)} = (f/A_\epsilon) - (B_\epsilon/A_\epsilon)^2. \qquad (9)$$

Although $B_\epsilon$ appears in the slope of Eq. (6) and can, in principle, be determined from pressure measurements by means of Eq. (5), the resultant value of $B_\epsilon$ remains one of limited accuracy. This is due to the fact that $B_\epsilon$ appears only in combination with $A_\epsilon B_p$, which is generally an order of magnitude larger. As such, a small error in the slope $(B_\epsilon - A_\epsilon B_p)$ could lead to a very large error in $B_\epsilon$.

More accurate values of $B_\epsilon$ can be obtained from a second series of measurements based on a cyclic expansion technique using the apparatus according to the invention, but without the solid in the sample cell. Initially the system is filled with gas, the valve is closed, and the dielectric constant $\epsilon_1$ is measured. The sample cell is then evacuated, the gas from the capacitance cell allowed to expand into the sample cell, the valve closed, and the dielectric constant $\epsilon_2$ is measured. The process is repeated a number of times giving a series of measurements of $f_i = (i - 1)(\epsilon_i + 2)^{-1}$ at a set of densities $d_i$ in fixed ratios r such that:

$$d_{(i+k)} = [V_C/(V_C+V_B)]^k d_i = r^k d_i.\quad(10)$$

Values of f after i and (i+k) expansions are, from Eq. (2), related by:

$$f_i/f_{(i+k)} = r^{-k} + (r^{-k}-1)(B_\epsilon/A_\epsilon^2)F_i + (r^{-k}-r^{-k})[(C_\epsilon/A_\epsilon^3)-(B_\epsilon^2/A_\epsilon^4)]f_i^2.\quad(11)$$

The quantities $r^{-k}$ and $(B_\epsilon/A_\epsilon^2)$ can be obtained by plotting the left-hand side of Eq. (11) vs. $f_i$.

Unlike the volumetric method which is limited by its depencency on the availability and reliability of the compressibility data for the gas to be studied, the method according to the invention is self-sufficient. That is, it determines the density of the adsorbate under the same experimental conditions as for the adsorption measurement. Moreover, when comparing the method of the invention with the volumetric method in the case of nonpolar gases, it should be pointed out that more than 99% of the contribution in the density comes from the first term ($f/A_\epsilon$). The remaining contribution of 1% comes from the second and higher-order terms in the dielectric virial series. It turns out that for nonpolar gases, the contribution of the second-order correction to the ideal gas law is much more important in the pressure virial series than in the dielectric virial series.

Thus, in the case of nonpolar gases, the method according to the invention becomes simple to apply especially when measuring adsorption as a function of temperature. First, $B_\epsilon$ does not have to be measured, and second, $A_\epsilon$ which is now temperature independent has to be measured only once during the course of the adsorption measurement.

In the case of polar gases or at very high pressures, the contribution of $B_\epsilon$ becomes noticeable and should be measured. This is simply done by means of the cyclic expansion technique described above and using the same apparatus. The precision of this technique is limited to about 10% which is generally acceptable for a second-order correction.

The method of determining the density of a gas through measurement of its dielectric constant is also novel and constitutes another aspect of the invention. Thus, according to still a further aspect of the invention, there is provided a method of determining the density of gas, which comprises filling a capacitance cell with the gas at a predetermined pressure and measuring the dielectric constant of the gas at the predetermined pressure to determine the density thereof.

If a first-order density approximation is desired, the first dielectric virial coefficient $A_\epsilon$ can be measured by varying the pressure of the gas in the capacitance cell and measuring the dielectric constant to the gas at different pressures to provide a first series of dielectric constant measurements from which $A_\epsilon$ is determined. Where a second-order density approximation is desired, the second dielectric virial coefficient $B_\epsilon$ can be measured by:

(a) allowing the gas from the capacitance cell to expand into a second evacuated cell in controlled gas flow communication with the capacitance cell, and measuring the dielectric constant of the gas at equilibrium pressure;

(b) evacuating the capacitance cell;

(c) allowing the gas from the second cell to expand into the capacitance cell and measuring the dielectric constant of the gas at a new equilibrium pressure;

(d) evacuating the second cell; and (e) repeating steps (a) through (d) at progressively decreasing pressures to provide a second series of dielectric constant measurements from which $B_\epsilon$ is determined.

Further features and advantages of the invention will become more readily apparent from the following description of preferred embodiments with reference to the appended drawings, in which.

Figure 1:
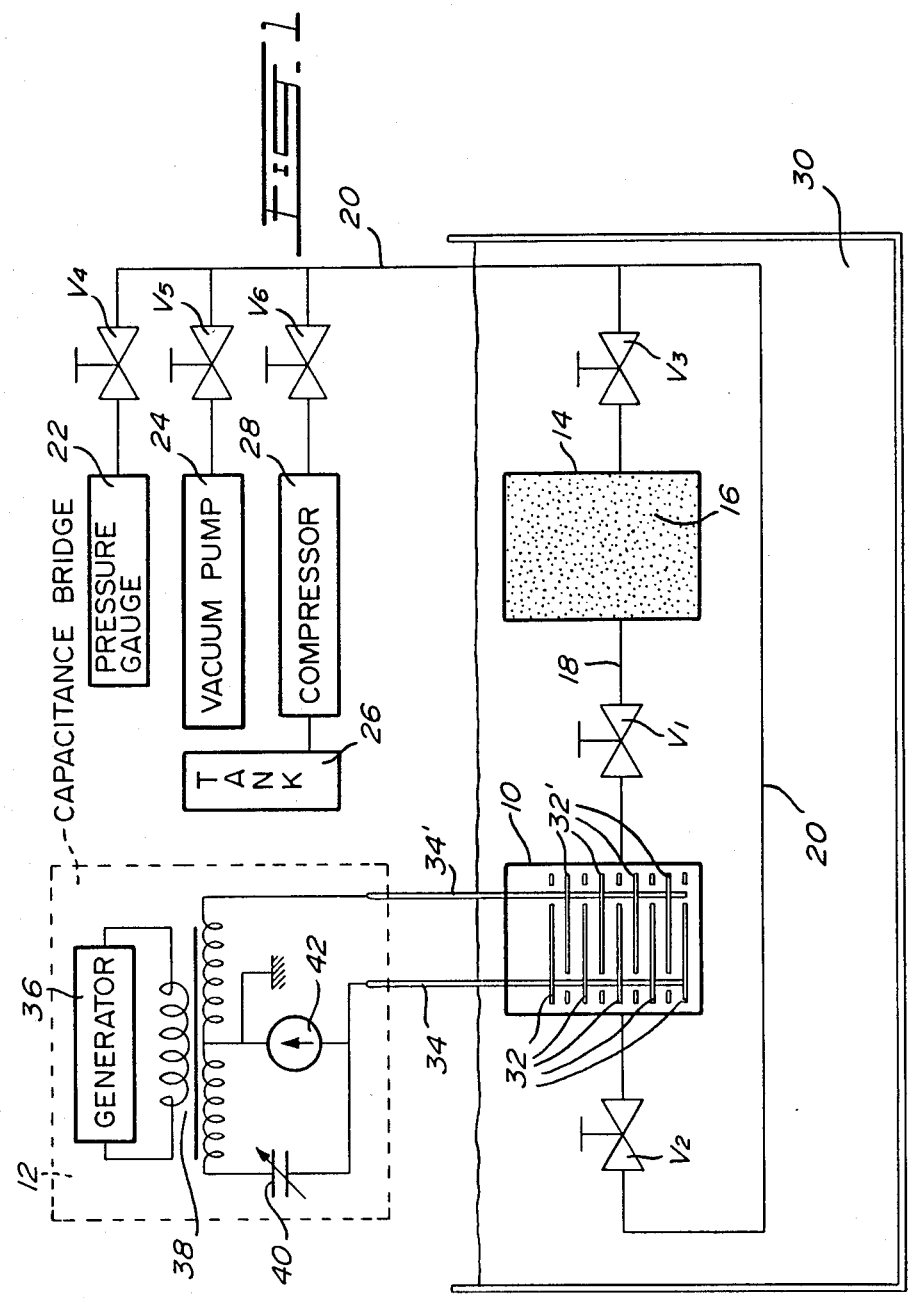
FIG. 1 is a schematic diagram of an apparatus according to a preferred embodiment of the invention.

As illustrated in FIG. 1, the apparatus used for effecting dielectric constant measurements comprises a three-terminal cylindrical capacitance cell 10 (only two terminals shown, the third terminal consisting essentially of a ground to eliminate capacitance fringing effects) connected to a capacitance bridge 12 which is a decade transformer bridge (General Radio type 1615-A) having a resolution of the order of $1\times10^{-17}$ F. (10 aF): and an accuracy at 1 kHz of ±0.01%. The capacitance cell 10 is in gas flow communication with a cylindrical sample cell 14 containing a solid adsorbent 16 by means of conduit 18, the flow of gas between the cells being controlled by valve $V_1$. The cell 10 is made of stainless steel and has a geometrical capacitance of 100.0±0.1 pF and a free volume $V_C$ of 96±1 ml. The sample cell 14 of volume $V_s$=146±1.5 ml is also made of stainless steel. Both cells are connected with high-pressure tubing 20 and suitable valves $V_2$, $V_3$, $V_4$, $V_5$ and $V_6$ to an external gas handling equipment including a pressure gauge 22, a vacuum pump 24, a tank 26 containing an adsorptive gas and a compressor 28 for compressing same. The assembly is immersed in a circulating bath 30 maintained at constant temperature by a proportional controller (not shown).

As shown, the capacitance cell 10 comprises a plurality of spaced-apart electrode members 32, 32' in the form of circular plates, each of the plates 32 being arranged alternatively with the plates 32' inside the cell with each plate 32 being connected to a conductor element 34 and each plate 32' connected to a conductor element 34', the conductor elements 34, 34' being in turn connected to the capacitance bridge 12. The plates 32 and 32' are spaced from one another to define a gap of about 2 to 5 mm, preferably 2 mm. The capacitance bridge 12 includes a frequency generator 36, a transformer 38, a variable capacitor 40 and a meter 42.

In order to determine the amount of gas adsorbed by the solid adsorbent 16 contained in the sample cell 14, both cells 10 and 14 are first evacuated by opening valves $V_1$, $V_2$, $V_3$ and $V_5$, the valve $V_6$ being closed; valve $V_4$ remains open during the entire experiment. When the system is under vacuum, valves $V_1$, $V_3$ and $V_5$ are closed and valve $V_6$ is opened so as to fill the capacitance cell 10 with the adsorptive gas at a predetermined pressure. Valve $V_2$ is closed and the dielectric constant of the gas is measured by means of the capacitance bridge 12. Valve $V_1$ is then opened to allow the gas from the capacitance cell 10 to expand into the sample cell 14 for adsorption by the adsorbent 16. As adsorption takes place, the pressure in the system falls until equilibrium is established. The dielectric constant of the gas at equilibrium pressure is measured and the densities of the gas before and after expansion are determined from these dielectric constant measurements. The amount of gas molecules adsorbed at the equilibrium pressure can thereafter be calculated using Eq. (1).

By repeating the above procedure at progressively increasing pressures until a pressure of about 1.2 MPa is reached, a series of dielectric constant measurements can be obtained from which the first dielectric virial coefficient $A_\epsilon$ can be determined.

The second dielectric virial coefficient $B_\epsilon$ can also be determined from a second series of dielectric constant measurements using the same apparatus as shown in FIG. 1, but without the solid adsorbent 16 in the sample cell 14. The capacitance cell 10 being initially filled with gas at a predetermined pressure and the valve $V_1$ closed, the dielectric constant is measured. The sample cell is evacuated, the valve $V_1$ is opened to allow the gas from the capacitance cell 10 to expand into the sample cell 14, and the dielectric constant of the gas at equilibrium pressure is measured. Valve $V_1$ is closed and the capacitance cell 10 is evacuated. The valve $V_1$ is again opened to allow the gas from the sample cell 14 to expand into the capacitance cell 10, and the dielectric constant of the gas at the new equilibrium pressure is measured. This procedure is repeated at progressively decreasing pressures until a pressure of a few atmospheres (about 0.2 MPa) is reached. The value of $B_\epsilon$ can then be determined from a plot of the left-hand side of Eq. (11) vs $f_i$.

The following non-limiting example further illustrates the invention.

EXAMPLE

Activated BPL-carbon from the Calgon Company was used as the adsorbent. The adsorbate was ultrahigh-purity methane supplied by Matheson with a stated purity of 99.97%. Degassing of the adsorbent was done under vacuum at 200° C. for 3 hr. The adsorbent was also degassed thoroughly after calibration of the dead space.

Isotherm measurements were done at 25° C. and pressures up to 16.5 MPa. In order to compare the dielectric method according to the invention with the volumetric method under the same experimental conditions, the pressure was measured in addition to the dielectric constant. Methane being nonpolar, Eq. (4) was used as the basis for calculating amounts of gas adsorbed in the dielectric method. The ideal gas law was used as the basis for the volumetric method. The correction for gas nonideality was done by using the compressibility factor Z calculated from the equation of state of methane at the measured pressure and temperature.

Figure 2:
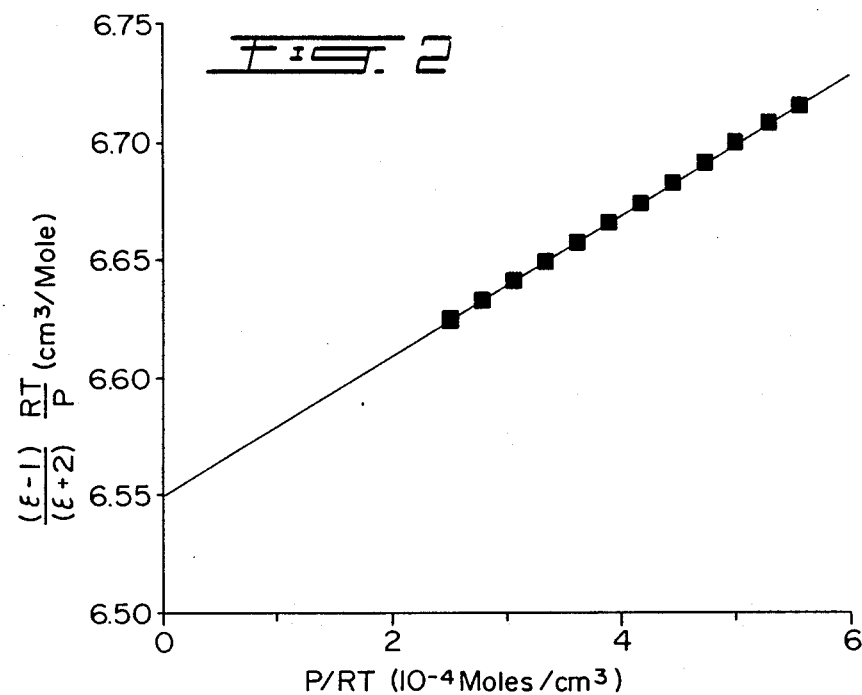
FIG. 2 shows a plot of $(\epsilon-1)(\epsilon+2)(RT/P)$ vs. $(P/RT)$ for methane at 25° C.

FIG. 2 shows a plot of the Clausius-Mossotti function at low pressure P ($<1.2$ MPa). $A_\epsilon$ found from the intercept of the curve has a value of 6.5489 $cm^3$ $mole^{-1}$ with a standard deviation of 0.00035 from the least-squares fit. The deviation corresponds to an error less than $2 \times 10^{-4}$ in $A_\epsilon$.

Figure 3:
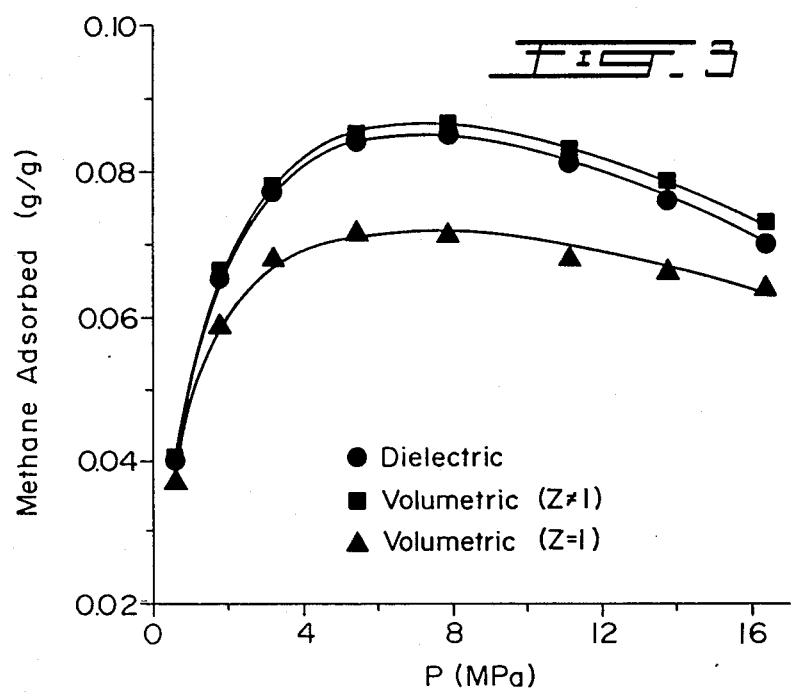
FIG. 3 shows the adsorption isotherms of methane on BPL-activated carbon.

FIG. 3 shows the adsorption isotherm obtained from dielectric measurements with $A_\epsilon$ determined in the same experiment and the isotherms obtained from pressure measurements with and without corrections for gas non-ideality. It can be easily seen that at low pressures, where the gas in the bulk phase behaves almost like an ideal gas, results from the dielectric method and the volumetric method are very close. However, as the pressure increases and the bulk phase starts deviating from ideality, adsorption increments given by the volumetric method before correction for nonideality become more and more erroneous. The error at 16.5 MPa is about 300%. It can also be seen from FIG. 3 that the agreement between the dielectric results and the volumetric results becomes quite good when the later are corrected for nonideality.

After completion of the first series of measurements, the adsorbent was removed, the sample cell was evacuated, and a second series of dielectric constant measurements was carried out at progressively decreasing densities until a pressure of a few atmospheres was reached. A binomial fit of the ratios $f_i/f_{(i+4)}$ vs $f_i$, [see Eq. (11)] gave a value $r^{-4}=4.324$ and a value $B_\epsilon=7.47\pm0.8$ $cm^6$ $mole^{-2}$. Values of the first-order density $d^{(1)}$ given by Eq. (4) and the second-order density $d^{(2)}$ given by Eq. (9) are listed in Table I hereinbelow with values of d calculated from the equation of state of methane at 25° C. and the measured pressure $P_m$; the pressure $P_c$ is calculated from the equation of state of methane at 25° C. and the measured density $d^{(1)}$,

TABLE 1

| $P_m$ (MPa) | $d^{(1)}$ (g/l) | $d^{(2)}$ (g/l) | d (g/l) | $P_c$ (MPa) |
|---|---|---|---|---|
| 0.524 | 3.577 | 3.576 | 3.422 | 0.530 |
| 1.738 | 11.76 | 11.75 | 11.59 | 1.763 |
| 3.172 | 21.77 | 21.74 | 21.69 | 3.184 |
| 5.400 | 38.43 | 38.33 | 38.34 | 5.412 |
| 7.890 | 58.39 | 58.15 | 58.27 | 7.908 |
| 11.138 | 85.96 | 85.43 | 85.75 | 11.166 |
| 13.759 | 108.7 | 107.8 | 108.3 | 13.821 |
| 16.386 | 130.4 | 129.2 | 129.9 | 16.452 |

Table I shows that contributions of $B_\epsilon$ to the density are less than 0.25%, 0.5% and 1% for respective pressures of 5, 10 and 16 MPa. The first-order equation is thus a valid representation of the density of nonpolar gases. Table I also lists values of pressure calculated from the equation of state of methane at the measured densities $d^{(1)}$ and temperature. The differences between the measured values and the ones calculated are well within the precision of the transducer used for measuring the pressure.

We claim:

1. A method of measuring physical adsorption of a gas by a solid adsorbent, wherein use is made of a capacitance cell in controlled gas flow communication with a sample cell initially under vacuum and containing the solid adsorbent, said method comprising the steps of:
    (a) filling said capacitance cell with an adsorptive gas at a predetermined pressure and measuring the dielectric constant of said gas at said predetermined pressure to determine a first density value;
    (b) allowing said gas from said capacitance cell to expand into said sample cell for adsorption by said solid adsorbent, whereby as adsorption takes place pressure falls until equilibrium is established;
    (c) measuring the dielectric constant of said gas at equilibrium pressure to determine a second density value; and
    (d) determining the amount of gas adsorbed by said solid adsorbent at said equilibrium pressure from said first and second density values.

2. A method according to claim 1, wherein said solid adsorbent defines in said sample cell a dead space volume and wherein said dead space volume is calibrated prior to step (a) by filling said capacitance cell with a non-adsorptive gas at an initial pressure, measuring the dielectric constant of said non-adsorptive gas at said initial pressure to determine an initial density value, allowing said non-adsorptive gas to expand from said capacitance cell into said sample cell, measuring the dielectric constant of said non-adsorptive gas at equilibrium pressure to determine a new density value and determining said dead space volume from said initial and new density values.

3. A method according to claim 2, wherein said non-adsorptive gas is helium.

4. A method according to claim 1, wherein steps (a) through (c) are repeated at progressively increasing pressures to provide a first series of dielectric constant measurements from which a first dielectric virial coefficient is determined.

5. A method according to claim 4, wherein steps (a) through (c) are repeated until a pressure of about 1.2 MPa is reached.

6. A method according to claim 4, further including the steps of:
(e) removing said adsorbent from said sample cell;
(f) evacuating said sample cell;
(g) allowing the adsorptive gas from said capacitance cell to expand into said sample cell and measuring the dielectric constant of said gas at equilibrium pressure;
(h) evacuating said capacitance cell;
(i) allowing the gas from said sample cell to expand into said capacitance cell and measuring the dielectric constant of said gas at a new equilibrium pressure; and
(j) repeating steps (f) through (i) at progressively decreasing pressures to provide a second series of dielectric constant measurements from which a second dielectric virial coefficient is determined.

7. A method according to claim 6, wherein steps (f) through (i) are repeated until a pressure of about 0.2 MPa is reached.

8. A method according to claim 1, wherein said capacitance cell and said sample cell are maintained at a substantially constant temperature.

9. A method according to claim 8, wherein said substantially constant temperature is about 25° C.

10. An apparatus for measuring physical adsorption of a gas by a solid adsorbent, comprising:
a capacitance cell having therein at least two electrode members arranged in opposite spaced-apart relation to one another, said electrode members being provided with connector means for connection to a capacitance bridge;
a sample cell for containing said solid adsorbent;
conduit means interconnecting said cell for allowing gas flow communication therebetween, said conduit means being provided with valve means for controlling the gas flow between said cells;
vacuum means connected to said sample cell for evacuating same; and
gas compressing means connected to said capacitance cell for filling same with an adsorptive gas at a predetermined pressure, whereby the adsorptive gas from said capacitance cell is allowed to expand into said sample cell for adsorption by said solid adsorbent and the dielectric constant of said gas is measured before and after expansion to determine the amount of gas adsorbed by said solid adsorbent.

11. An apparatus according to claim 10, wherein said electrode members are plate members and said connector means comprise a pair of conductor elements, and wherein said capacitance cell comprises a plurality of spaced-apart first and second plate members, each of said first plate members being arranged alternatively with said second plate members inside said capacitance cell with each said first plate member being connected to one of said conductor elements and each said second plate member connected to the other conductor element.

12. An apparatus according to claim 11, wherein said first and second plate members are spaced from one another to define a gap of about 2 to 5 mm.

13. An apparatus according to claim 12, wherein said gap is about 2 mm.

14. An apparatus according to claim 10, wherein said capacitance cell has a geometrical capacitance of $100.0 \pm 0.1$ pF.

15. An apparatus according to claim 10, wherein said capacitance bridge comprises a decade transformer bridge.

16. An apparatus according to claim 15, wherein said decade transformer bridge has a resolution of the order of $1 \times 10^{-17}$ F.

17. An apparatus according to claim 15, wherein said decade transformer bridge has an accuracy at 1 kHz of $\pm 0.01\%$.

18. A method of determining the density of a gas, which comprises filling a capacitance cell with the gas at a predetermined pressure, measuring the dielectric constant of said gas at said predetermined pressure, varying the pressure of the gas in said capacitance cell and measuring the dielectric constant of said gas at different pressures to provide a first series of dielectric constant measurements from which a first dielectric virial coefficient is determined, to obtain a first-order density approximation.

19. A method according to claim 18, further including the steps of:
(a) allowing the gas from said capacitance cell to expand into a second evacuated cell in controlled gas flow communication with said capacitance cell, and measuring the dielectric constant of said gas at equilibrium pressure;
(b) evacuating said capacitance cell;
(c) allowing the gas from said second cell to expand into said capacitance cell and measuring the dielectric constant of said gas at a new equilibrium pressure;
(d) evacuating said second cell; and
(e) repeating steps (a) through (d) at progressively decreasing pressures to provide a second series of dielectric constant measurements from which a second dielectric virial coefficient is determined to obtain a second-order density approximation.

* * * * *

UNITED STATES PATENT AND TRADEMARK OFFICE
CERTIFICATE OF CORRECTION

PATENT NO. : 4,856,320
DATED : August 15, 1989
INVENTOR(S) : Tapan K. Bose, et al It is certified that error appears in the above-identified patent and that said Letters Patent is hereby corrected as shown below:

Column 3, line 45, equation (2) should read $$-- CM = (\varepsilon-1)[(\varepsilon+2)d]^{-1} = A_\varepsilon + B_\varepsilon d + C_\varepsilon d^2 + \ldots, --$$

Column 4, line 4, equation (3) should read $$-- (\varepsilon-1)(\varepsilon+2)^{-1} \approx A_\varepsilon d, --$$

Column 4, line 16, equation (5) should read $$-- P(RTd)^{-1} = 1 + B_p d + C_p d^2 + \ldots, --$$

Column 4, lines 22-23, equation (6) should read $$-- (\varepsilon-1)(\varepsilon+2)^{-1}(RT/P) = A_\varepsilon + (B_\varepsilon - A_\varepsilon B_p)(P/RT) + \ldots . --$$

Column 4, line 24, "$(\varepsilon + 2)$" should read $$-- (\varepsilon+2)^{-1} --$$

UNITED STATES PATENT AND TRADEMARK OFFICE
CERTIFICATE OF CORRECTION

PATENT NO. : 4,856,320
DATED : August 15, 1989
INVENTOR(S) : Tapan K. Bose, et al It is certified that error appears in the above-indentified patent and that said Letters Patent is hereby corrected as shown below:

Column 4, line 25, "$(B_\varepsilon - A_\varepsilon B_p)$" should read

-- $(B_\varepsilon - A_\varepsilon B_p)$ --

Column 4, line 36, "$Be_\varepsilon$" should read -- $B_\varepsilon$ --

Column 4, line 39, equation (7) should read

-- $CM = (\varepsilon-1)/[(\varepsilon+2)d] \approx A_\varepsilon + B_\varepsilon d$ --

Column 4, line 48, equation (9) should read

-- $d^{(2)} = (f/A_\varepsilon) - (B_\varepsilon/A_\varepsilon)(f/A_\varepsilon)^2$ --

Column 4, line 67, "(i-1)" should read -- $(\varepsilon_i - 1)$ --

UNITED STATES PATENT AND TRADEMARK OFFICE
CERTIFICATE OF CORRECTION

PATENT NO. : 4,856,320

DATED : August 15, 1989

INVENTOR(S) : Tapan K. Bose, et al

It is certified that error appears in the above-identified patent and that said Letters Patent is hereby corrected as shown below:

Column 5, lines 2-7 should read

--Values of $f$ after i and (i + k) expansions are, from Eq. (2), related by:--

Column 5, line 8, equation (11) should read $$-\!-f_i/f_{(i+k)} = r^{-k} + (r^{-k}-1)(B_\varepsilon/A_\varepsilon^2)f_i + (r^{-k} - r^k)[(C_\varepsilon/A_\varepsilon^3) - (B_\varepsilon^2/A_\varepsilon^4)]f_i^2.-\!-$$

Column 5, lines 9-16 should read

--The quantities $r^{-k}$ and $(B_\varepsilon/A_\varepsilon^2)$ can be obtained by plotting the left-hand side of Eq. (11) vs $f_i$--

UNITED STATES PATENT AND TRADEMARK OFFICE
CERTIFICATE OF CORRECTION

PATENT NO. : 4,856,320
DATED : August 15, 1989
INVENTOR(S) : Tapan K. Bose, et al It is certified that error appears in the above-indentified patent and that said Letters Patent is hereby corrected as shown below:

Column 6, line 18, "$(\varepsilon+2)$" should read --$(\varepsilon+2)^{-1}$--.

Signed and Sealed this

Twenty-sixth Day of October, 1993

Attest:

BRUCE LEHMAN

Attesting Officer

Commissioner of Patents and Trademarks